United States Patent
Lee et al.

(10) Patent No.: US 6,241,994 B1
(45) Date of Patent: Jun. 5, 2001

(54) SOLID TCMTB FORMULATIONS

(75) Inventors: James C. Lee; Luis Fernando Del Corral, both of Memphis; Richard A. Clark, Collierville; Pedro A. Bonilla, Memphis, all of TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

(21) Appl. No.: 09/031,829

(22) Filed: Feb. 27, 1998

(51) Int. Cl.$^7$ .................................................. A01N 25/34
(52) U.S. Cl. ........................... 424/408; 424/404; 424/405
(58) Field of Search ..................................... 424/404, 405, 424/408

(56) References Cited

U.S. PATENT DOCUMENTS

| | | | |
|---|---|---|---|
| 3,198,740 | 8/1965 | Dunlop et al. | 252/90 |
| 3,520,976 | 7/1970 | Buckman et al. | 424/270 |
| 3,929,678 | 12/1975 | Laughlin et al. | 252/526 |
| 3,985,669 | 10/1976 | Krummel et al. | 252/116 |
| 4,293,559 | 10/1981 | Buckman et al. | 424/270 |
| 4,310,434 | 1/1982 | Choy et al. | 252/174.21 |
| 4,477,363 | 10/1984 | Wong et al. | 252/134 |
| 4,479,961 | 10/1984 | Martin | 424/270 |
| 4,595,691 | 6/1986 | LaMarre et al. | 514/367 |
| 4,839,373 | 6/1989 | Ito et al. | 514/367 |
| 4,866,081 | 9/1989 | Ito et al. | 514/367 |
| 4,944,892 | 7/1990 | Leathers et al. | 252/92 |
| 5,043,090 | 8/1991 | Camp et al. | 252/106 |
| 5,234,615 | 8/1993 | Gladfelter et al. | 252/90 |
| 5,235,615 | 8/1993 | Omura | 375/1 |
| 5,413,795 * | 5/1995 | Lee et al. | 424/489 |
| 5,614,484 | 3/1997 | Panandiker | 510/102 |
| 5,637,308 | 6/1997 | Del Corral et al. | 424/409 |
| 5,707,534 | 1/1998 | Del Corral et al. | 210/755 |
| 5,709,880 | 1/1998 | Del Corral et al. | 424/464 |

\* cited by examiner

Primary Examiner—José G. Dees
Assistant Examiner—Konata M. George
(74) Attorney, Agent, or Firm—Morgan, Lewis & Bockius LLP

(57) ABSTRACT

The invention provides a solid TCMTB formulation for controlling the growth of at least one microorganism. The use of a solid TCMTB formulation, as compared to a liquid, minimizes user contact and is more readily packaged. A solid TCMTB formulation of the invention contains TCMTB adsorbed onto a water-soluble, salt carrier matrix, with the TCMTB present in an amount effective to control the growth of at least one microorganism, preferably in an aqueous system. Other microbicides and additives may also be incorporated into a solid TCMTB formulation of the invention. In a preferred embodiment, the formulation contains both TCMTB and one or more other microbicides (e.g., methylene bisthiocyanate (MTC)) and a water-soluble, salt carrier matrix. The TCMTB is adsorbed onto the water-soluble salt carrier matrix. The TCMTB and other microbicide are present in a combined antimicrobial amount effective for the control of at least one microorganism. A solid TCMTB formulation may be used in a wide variety of biocide applications. Accordingly, the invention also relates to a method for controlling the growth of at least one microorganism in a liquid, preferably aqueous, system. In particular, the method controls the growth of at least one microorganism in an aqueous system by contacting an aqueous system with a solid TCMTB formulation comprising TCMTB adsorbed onto a water-soluble salt carrier matrix in an amount effective to control the growth of at least one microorganism in the aqueous system.

22 Claims, 1 Drawing Sheet

COMPARATIVE ANTI-BACTERIAL EFFICACY BETWEEN SOLID AND LIQUID FORMULATIONS OF MTC/TCMTB

4 HOURS CONTACT TIME IN SYNTHETIC COOLING TOWER WATER
(pH 8.5)

SOLID TCMTB FORMULATIONS

FIELD OF THE INVENTION

The invention relates to a solid formulation of 2-(thiocyanomethylthio)-benzothiazole (TCMTB) useful for controlling the growth of microorganisms. More particularly, the invention relates to a solid TCMTB formulation where TCMTB is absorbed onto a water-soluble, salt carrier matrix. A solid TCMTB formulation of the invention is particularly useful in treating a variety of systems experiencing unwanted biological growth, particularly microbiological growth.

BACKGROUND OF THE INVENTION

A variety of industries are subject to problems occurring with the growth of microorganisms including the leather industry, the lumber industry, the textile industry, the agriculture industry and the coating industry. In particular, biofouling, or biological fouling, is a persistent nuisance or problem in a wide varieties of aqueous industrial systems. Biofouling, both microbiological and macrobiological fouling, is caused by the buildup, of microorganisms, macroorganisms, extracellular substances, and dirt and debris. The organisms involved include microorganisms such as bacteria, fungi, yeasts, algae, diatoms, protozoa, and macroorganisms such as macroalgae, barnacles, and small mollusks like Asiatic clams or Zebra Mussels.

Another objectionable biofouling phenomenon, that of slime formation, occurs in aqueous systems. Slime formation can occur in fresh, brackish or salt water systems. Slime consists of matted deposits of microorganisms, fibers and debris. It may be stringy, pasty, rubbery, tapioca-like, or hard, and have a characteristic, undesirable odor that is different from that of the aqueous system in which it formed. The microorganisms involved in slime formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms.

Biofouling, which often degrades an aqueous system, may manifest itself as a variety of problems, such as loss of viscosity, gas formation, objectionable odors, decreased pH, color change, and gelling. Additionally, degradation of an aqueous system can cause fouling of the related water-handling system, which may include, for example, cooling towers, pumps, heat exchangers, and pipelines, heating systems, scrubbing systems, and other similar systems.

Biofouling can have a direct adverse economic impact when it occurs in industrial process waters, for example in cooling waters, metal working fluids, or other recirculating water systems such as those used in papermaking or textile manufacture. If not controlled, biological fouling of industrial process waters can interfere with process operations, lowering process efficiency, wasting energy, plugging the water-handling system, and even degrade product quality.

For example, cooling water systems used in power plants, refineries, chemical plants, air-conditioning systems, and other industrial operations frequently encounter biofouling problems. Airborne organisms entrained from cooling towers as well as waterborne organisms from the system's water supply commonly contaminate these aqueous systems. The water in such systems generally provides an excellent growth medium for these organisms. Aerobic and heliotropic organisms flourish in the towers. Other organisms grow in and colonize such areas as the tower sump, pipelines, heat exchangers, etc. If not controlled, the resulting biofouling can plug the towers, block pipelines, and coat heat-transfer surfaces with layers of slime and other biologic mats. This prevents proper operation, reduces cooling efficiency and, perhaps more importantly, increases the costs of the overall process.

Industrial processes subject to biofouling also include papermaking, the manufacture of pulp, paper, paperboard, etc. and textile manufacture, particularly water-laid nonwoven textiles. These industrial processes generally recirculate large amounts of water under conditions which favor the growth of biofouling organisms.

Paper machines, for example, handle very large volumes of water in recirculating systems called "white water systems." The furnish to a paper machine typically contains only about 0.5% of fibrous and non-fibrous papermaking solids, which means that for each ton of paper almost 200 tons of water pass through the headbox. Most of this water recirculates in the white water system. White water systems provide excellent growth media for biofouling microorganisms. That growth can result in the formation of slime and other deposits in headboxes, waterlines, and papermaking equipment. Such biofouling not only can interfere with water and stock flows, but when loose, can cause spots, holes, and bad odors in the paper as well as web breaks—costly disruptions in paper machine operations.

Sanitation waters, like industrial process waters, are also vulnerable to biofouling and its associated problems. Sanitation waters include toilet water, cistern water, septic water, and sewage treatment waters. Due to the nature of the waste contained in sanitation waters, these water systems are particularly susceptible to biofouling.

Liquid formulations, containing the microbicide 2-(thiocyanomethylthio)-benzothiazole (TCMTB), are known in the art and have often been used to control or prevent biological fouling, including biofilm and slime formation, in aqueous systems. TCMTB emulsifiable concentrates offer the advantage of easy application but suffer from disadvantages including strong skin irritation, freezing at cold temperatures, foul odor and precipitation of the active ingredient. Additionally, as concerns about environmental protection mount, efforts are being directed to reducing the volatile organic concentration (VOC) of biocides used in the treatment of industrial aqueous systems.

Solid formulations provide many advantages over liquid formulations. One such solid formulation is described in U.S. Pat. No. 5,413,795, incorporated by reference herein in its entirety. In U.S. Pat. No. 5,413,795, a solid TCMTB formulation was made having TCMTB adsorbed onto a water insoluble solid carrier.

Well formulated solid forms provide increased stability and reduce exposure to chemicals, solvents, or vapors. In a solid, different ingredients may be successfully combined where such a combination in a liquid might lead to unwanted reactions and potential loss of activity. Using a solid form, a chemical formulation can often be packaged and shipped in a more concentrated form than with liquid formulations. Solid forms are more easily contained within water-soluble packaging. Solid forms can also reduce or eliminate concerns regarding the liquid spilling or containers breaking during shipping or handling.

At the point of use, solid forms may also offer additional advantages over liquid formulations. Solid forms provide unit dosing and a uniform delivery system which aids in controlling the amounts used. Solid forms of water treatment chemicals can also be formulated to provide sustained or prolonged release of chemicals to the aqueous system.

SUMMARY OF THE INVENTION

The invention answers the problems arising from the use of liquid microbicide formulations by providing a solid TCMTB formulation which minimizes user contact and is more readily packaged. A solid TCMTB formulation of the invention contains TCMTB adsorbed onto a water-soluble, salt carrier matrix, with the TCMTB present in an amount effective to control the growth of at least one microorganism, preferably in an aqueous system. Other microbicides and additives may also be incorporated into a solid TCMTB formulation of the invention. In a preferred embodiment, the formulation contains both TCMTB and one or more other microbicides (e.g., methylene bisthiocyanate (MTC)) and a water-soluble, salt carrier matrix. The TCMTB is adsorbed onto the water-soluble salt carrier matrix. The TCMTB and other microbicide are present in a combined antimicrobial amount effective for the control of at least one microorganism.

The solid formulations of the invention may be made by mixing TCMTB with a water-soluble, salt carrier matrix to form a powder. When mixing the TCMTB and the salt carrier matrix, the TCMTB may be in liquid form while the salt carrier matrix is generally a solid. The powder may be granulated, if necessary, to reduce the powder to the desired particle size. If tablets are desired, the solid TCMTB powder formulation may be tabletized to form a tablet.

The solid formulations of the invention may be used in a wide variety of biocide applications. Accordingly, the invention also relates to a method for controlling the growth of at least one microorganism in a liquid, preferably aqueous, system. In particular, the method controls the growth of at least one microorganism in an aqueous system by treating an aqueous system with a solid TCMTB formulation comprising TCMTB adsorbed onto a water-soluble salt carrier matrix in an amount effective to control the growth of at least one microorganism in the aqueous system.

In another embodiment, the invention relates to a method of controlling the growth of at least one microorganism on a substrate susceptible to the growth of microorganism. The method of treating a substrate to control the growth of at least one microorganism involves contacting a liquid system with a formulation comprising TCMTB adsorbed onto a water-soluble salt carrier matrix to form a liquid TCMTB formulation in amount effective to control the growth of at least one microorganism of followed by treating the substrate with the liquid TCMTB formulation.

DETAILED DESCRIPTION OF THE INVENTION

Figure 1:
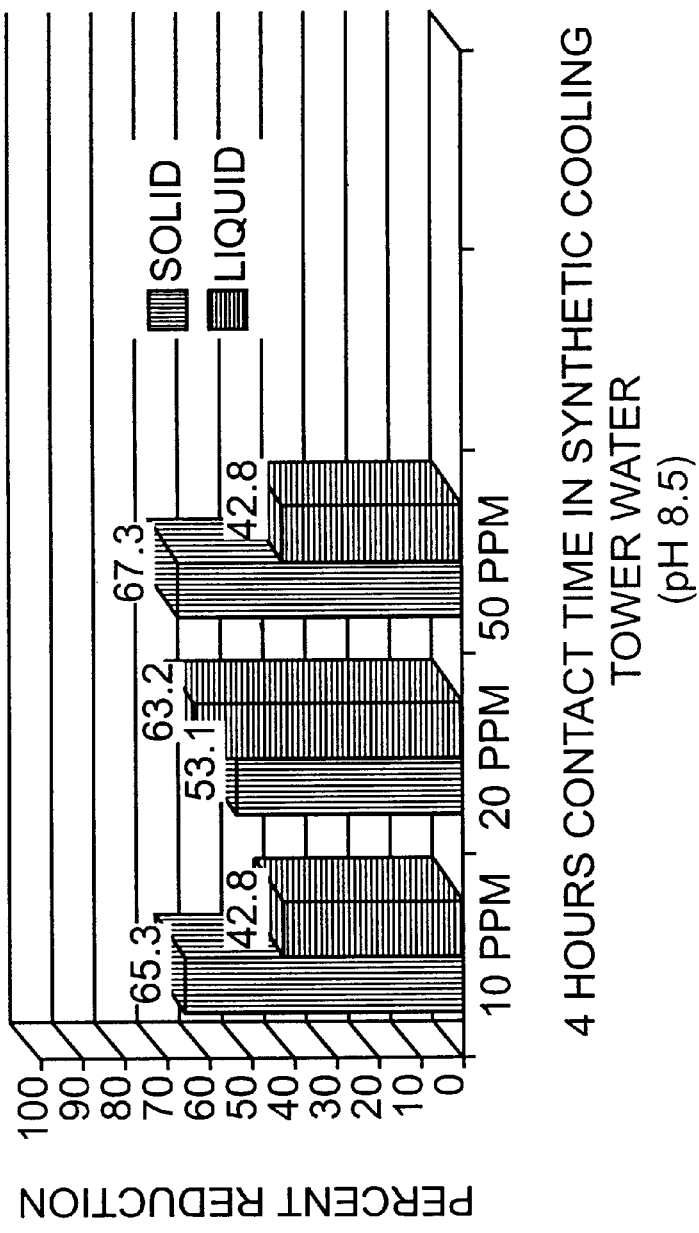
FIG. 1 is a diagram of the results obtained in Example 1.

One embodiment of the invention relates to a solid TCMTB formulation useful for controlling the growth of microorganisms. The formulation comprises TCMTB adsorbed onto a water-soluble, salt carrier matrix. The formulation contains an effective amount of TCMTB to control the growth of at least one microorganism. Solid TCMTB formulations of the invention are particularly useful in controlling the growth of microorganisms in an aqueous system, as well as reducing or eliminating the problems associated with microbiological growth, particularly those described above. Examples of various aqueous systems are discussed below. An "aqueous system" may contain other liquids or components in addition to water. A solid TCMTB formulation of the invention may be in the form of a powder or a tablet. A tablet may be prepared by tabletizing or compressing the powder. Due to their ability to disperse quickly in an aqueous system, and their less costly preparation, powder formulations are generally preferred.

To control the growth of at least one microorganism, the solid formulation comprises a microbiocidally effective amount of TCMTB, preferably an amount ranging from about 0.1% to about 60% by weight based on the total weight of the formulation. More preferably, the amount of TCMTB ranges from 1 to 40%, even more preferably from 5 to 30% by weight and most preferably from 5 to 20% by weight. The formulation may contain from about 40% to about 99.9% by weight of the salt carrier matrix based on the total weight of the formulation. Preferably, the amount of salt carrier matrix ranges from 60% to 99%, even more preferably from 70% to 95% by weight and most preferably from 80 to 95%.

According to the present invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The solid TCMTB formulation described here can, in many cases, reduce the total microbiological count to undetectable limits and maintain the count at that level for a significant period of time. Accordingly, the solid TCMTB formulations of the invention may be used to preserve a substrate or system.

TCMTB

The microbicidal properties of 2-(thiocyanomethylthio) benzothiazole (TCMTB) are well-known. TCMTB has been used for industrial microorganism control for over 20 years. TCMTB is known to be useful in controlling bacteria and fungi in various aqueous systems. The preparation and use of 2-(thiocyanomethylthio)-benzothiazole as a microbicide and a preservative is described in U.S. Pat. Nos. 3,520,976, 4,293,559, 4,866,081, 4,595,691, 4,944,892, 4,839,373, and 4,479,961 which give examples of the microbicidal properties of 2-(thiocyanomethylthio)benzothiazole. The disclosures of all of these patents are incorporated herein by reference in their entirety.

TCMTB is a pH sensitive compound. TCMTB may undergo decomposition at a pH above 8.0. Thus, it is preferred to employ a solid TCMTB formulation in a water treatment system having a pH of about 8.0 or less, more preferably a pH of about 7.0 or less. TCMTB is also relatively water insoluble (the solubility in water is about 0.033 g/l in water) and has a density of 1.38 g/ml. TCMTB is a solid in the pure form at room temperatures and in liquid form when mixed with an appropriate amount of solvent. TCMTB readily assumes an oily globular form in water even when it is emulsified.

TCMTB is a heat-sensitive compound with pure TCMTB forming a solid at room temperature. Because of its relative insolubility in water, TCMTB has been formulated mainly as an emulsifiable concentrate or as a water-based product. TCMTB is commercially available, for example, TCMTB formulations are available from Buckman Laboratories, Inc., Memphis, TN, under the BUSAN® 30WB, BUSAN® 1030, and BUSAN® 1118 trade names. In a preferred embodiment TCMTB-80 is used in the solid TCMTB formulations of the invention. TCMTB-80 is a viscose liquid at room temperature and may crystallize at room temperature in storage. The use of TCMTB-80 aids in the reduction of the amount of solvent used to formulate the solid TCMTB formulation. However, when formulating a solid TCMTB formulation with TCMTB-80 at cold temperatures it may be necessary to heat the TCMTB-80 to reduce its viscosity. Also, TCMTB-60 may be used in the invention. TCMTB-60 is TCMTB-80 which has been diluted with dipropylene glycol monomethyl ether. Both TCMTB-80 and TCMTB-60 are commercially available from Buckman Laboratories, Inc., Memphis, Tenn.

Salt Carrier Matrix

The water-soluble, salt carrier matrix material may be a single salt material or a mixture of two or more salts, alone or in combination with other matrix materials. When the carrier matrix contains a mixture of water-soluble salts, those salts are preferably present in equal amounts, e.g., a mixture of two salts in a 1:1 ratio. Generally, the salt carrier matrix should be in granular or powder form. The particle size of the carrier matrix powder or granules may vary depending upon the particular formulation and its intended use.

As described above, a solid TCMTB formulation of the invention contains a water-soluble, salt carrier matrix. When a solid formulation of the invention is used to treat an aqueous system, the salt carrier matrix substantially, if not completely, dissolves in the aqueous system leaving little or no solid residue. This is a particular advantage over using water insoluble carriers which may leave residue and/or damage the material or aqueous system being treated. Different salt carrier matrices may be used in different systems to achieve maximum dissolution in a particular aqueous system. Preferably, the salt carrier matrix is a water-soluble inorganic or organic salt or a mixture of such salts. For purposes of the present invention, water-soluble means having a solubility in water of at least about 0.2 grams per hundred grams of water at 20° C. Additionally, when selecting an appropriate carrier, the carrier is preferably not a nutrient for microorganisms. For example sugars, such as glucose and lactose, may not be suitable for some applications as they are known to be nutrients for various microorganisms, e.g., fungi and bacteria.

Examples of suitable salts for the carrier matrix include various alkali metal and/or alkaline earth metal sulfates, chlorides, borates, bromides, citrates, acetates, lactates, etc. Specific examples of suitable salts include, but are not limited to, sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate and lithium chloride. The preferred salts are the inorganic salts, especially the Group I or II metal sulfates and chlorides. Particularly preferred salts, because of their low cost, are sodium sulfate, and sodium chloride. The sodium chloride used in the invention may be substantially pure or in the form of rock salt, sea salt, or dendrite salt.

Emulsifiers

An emulsifier may be added to a solid TCMTB formulation to further improve the dispersibility of the TCMTB in an aqueous system. TCMTB is a relatively water insoluble compound, exhibiting a water solubility of about 0.033 g/l. Typically, an emulsifier may be present in the solid TCMTB formulations in amounts up to about 20 percent by weight of the solid formulation, preferably up to about 10 percent by weight of the formulation, more preferably up to about 5 percent by weight of the formulation and most preferably up to about 2 percent by weight of the formulation. Suitable emulsifiers for the solid TCMTB formulation include anionic, nonionic, amphoteric and zwitterionic surfactants and mixtures thereof. Preferably the emulsifier is anionic or nonionic or a mixture thereof.

Suitable anionic surfactants for solid TCMTB formulations include, but are not limited to, alkyl benzene sulphonates, alkyl sulfates, alkyl ether sulphonates, alkyl phenol sulphonates, alkyl phosphates, alkyl polyethoxylate carboxylates. There are other commercial available products which can work as well, including but not limited to, alkyl napthalene sulfonates, alkyl sulfosuccinate, sodium salt of polymerized alkyl naphthalene sulfonic acids, sodium naphthalene sulfonic acid formaldehyde, modified sodium or ammonium lignosulfonate, fatty sulfoesters, fatty sulfoamide, Witconate LX Powder (Witco Corporation, Greenwich, Conn.) and Rhodacal DS-10 (from Rhone-Poulenc, Cranbury, N.J.). However, the use of anionic surfactants which react and degrade the TCMTB, such as small alkyl chain anionic surfactants, should be avoided. Typically, the alkyl group in the anionic surfactant contains from 8 to 22 carbon atoms. Preferably the anionic surfactant is a $C_{12}$–$C_{20}$ alkyl sulfate, $C_{12}$–$C_{20}$ alkyl ether sulfate and/or $C_9$–$C_{20}$ linear alkyl benzene sulfonate with sodium salts. More preferably the anionic surfactant is a $C_9$–$C_{15}$ linear alkyl benzene sulfonate. Most preferably, the anionic surfactant is a calcium or sodium salt of dodecylbenzene sulfonate which are commercially available under the tradenames Casul 70 HF and Stepwet DF 90 which is a product from Stepan company, Northfield, Ill.

Suitable nonionic detergent surfactants are generally disclosed in U.S. Pat. No. 3,929,678, Laughlin et al., incorporated herein by reference in its entirety. Suitable nonionic surfactants include alkoxylated alcohols such as alkoxylated phenols, condensation products of ethylene oxide with a hydrophobic base formed by the condensation of propylene oxide with propylene glycol which may be end caped with an alkyl group, the condensation products of ethylene oxide with the product resulting from the reaction of propylene oxide and ethylenediamine and semi-polar nonionics, such as amine oxides, fatty acid amides, polyhydroxy amides, and alkyl polysaccharides including alkyl polyglycosides. The preferred nonionic surfactant is a block copolymer formed from ethylene oxide and propylene oxide and optionally capped on one or both terminal ends with an alkyl group. The most preferred nonionic surfactant is a block copolymer of ethyleneoxide and propyleneoxide reacted with butanol which is commercially available under the tradename Tergitol XD.

Zwitterionic surfactants include those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxyl, sulfonate, sulfate, phosphate, or phosphorate.

Examples of amphoteric surfactants which can be used in the formulations of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate.

Further examples are given in "Surface Active Agents and Detergents" Vol. I and II by Schwartz, Perry and Berch which is incorporated here by reference in its entirety. Also, many additional nonsoap emulsifiers are described in McCUTCHEON'S, DETERGENTS AND EMULSIFIERS, 1996 ANNUAL, published by Allured Publishing Corporation, which is incorporated here by reference in its entirety. A variety of such surfactants are also generally disclosed in U.S. Pat. No. 3,929,678, issued Dec. 30, 1975 to Laughlin, et al. at Column 23, line 58 through Column 29, line 23 and U.S. Pat. No. 5,614,484, Panandiker which are herein incorporated by reference in their entirety.

In a preferred embodiment of the invention the emulsifier is a mixture of ethylene oxide/propylene oxide copolymer and dodecyl benzene sulfonate.

Biocidal Adjuvants

The tablets of the invention may contain other biocidal adjuvants commonly used in water treatment. Such adjuvants include, for example, germicides, fungicides, sanitizers, and oxidizing and/or halogen-release agents as well as water clarifiers. These biocidal adjuvants may be present from 0 to about 50 percent by weight of the tablet. More preferably, they are present from about 5 to about 40 percent by weight of the tablet and most preferably about 10 to about 30 percent. The biocidal adjuvants may be in a liquid or solid form and is preferably a solid. Biocidal adjuvants used in the solid TCMTB formulation should not promote undesirable interactions with the TCMTB or other components in the solid TCMTB formulation.

Suitable germicides include, for example, formaldehyde release agents such as 1,3,5,7-tetra-aza-adamantine hexamethylenetetramine, chlorinated phenols, 1,3,5-tris(ethyl)hexahydro-s-triazine, hexahydro-1,3,5-tris(2-hydroxyethyl)-s-triazine, 1,3-(dihydroxymethyl)-5,5-dimethylhydantoin, N-methylolchloroacetamide, and the like. Hexahydro-1,3,5-tris-(2-hydroxyethyl)-s-triazine is available from Buckman Laboratories, Memphis, Tenn. as BUSAN® 1060 product, a 78.5 percent active solid formulation.

The oxidizing and/or halogen-release agents which can be used in connection with the present invention include, for example, N-chlorinated cyanuric acid derivatives such as sodium dichloroisocyanurate, N-chlorosuccinimide, Chloramine T. dichlorosuccinimide, bromochlorodimethylhydantoin, and 1,3-dichloro 5,5-dimethylhydantoin.

Other biocidal adjuvants include potassium n-hydroxymethyl-N-methyl thiocarbamate, a 30% active ingredient in BUSAN® 52 product, 30% active ingredient; and MECT 5 product, a mixture of 2.5 by weight and 2.5 percent by weight TCMTB. Each of these products is available from Buckman Laboratories, Memphis, Tenn. Chlorhexidine diacetate, another biocidal adjuvant, is the chemical 1,1-hexamethylenebis-[5-(4-chloro-2-phenyl)biguanide] diacetate available from Lonza Chemical Co., Fairlawn, N.J. The biocide BTC 2125MP40 product may also be used. BTC 2125MP40 product contains 40 percent of a mixture of alkyldimethylbenzoammonium chloride and alkyldimethylethylbenzoammonium chloride and is available from Stepan Chemicals, Northfield, Ill. Another suitable biocidal adjuvant is BTC 1100R which has cold water solubility up to 1500 ppm, and is available from Onyx Chemical Co. However, when using additional biocidal adjuvants, the adjuvants should be selected such that they do not degrade the TCMTB below its desired biocidal level.

In a preferred embodiment, MTC (methylene bisthiocyanate and also known as MTB), which acts as an antibacterial agent, is added to a solid TCMTB formulation. The addition of the MTC complements the antifungal properties of TCMTB and provides additional antimicrobial treatment properties to a solid TCMTB formulation. MTC has a melting point of 105° C., and a density of 2.0 g/ml. At room temperature it is a yellow crystalline solid with a characteristic odor MTC is considered unstable at temperatures greater than 100° C. The solubility of MTC in water is 5.0 g/l and it is soluble in most of organic solvents. MTC is stable in acidic systems at ambient temperature, however, MTC will decompose in alkaline solutions at a pH above 7.5. Consequently, it is preferred to employ solid TCMTB formulations containing MTC in water treatment systems having a pH of about 7.5 or less, more preferably 7.0 or less. The solubility of MTC in water is about 5 g/l allowing MTC to be added to the solid TCMTB formulation without the use of additional solvents and emulsifiers.

Other Additives

A solid TCMTB formulation of the invention may also contain additives known in the art to improve the solid formulation itself, its handling, or its use in the aqueous system. For example, additives such as wetting agents, dispersing agents, anti-caking agents and anti-foaming agents may also be used. Examples of such additives can be found in McCutcheon's publication "Emulsifiers & Detergents, Functional Materials", which is specifically incorporated by reference in its entirety. Typically, additives may each be present in the solid TCMTB formulations in amounts up to about 30 percent by weight of the solid formulation. Some of these conventional additives are discussed in more detail below.

A solid TCMTB formulation according to the invention may contain solid organic acids or their salts, such as benzoic, gluconic, or sorbic acid, incorporated in the salt carrier matrix. Use of such organic acids or their salts allows the salt carrier matrix to itself have beneficial activity, including biological activity, in the aqueous system. For example, gluconic acid, or its salts, may be used in a carrier matrix.

Conventional water clarifiers may also be included in a solid TCMTB of the invention. Clarifiers include, for example, polyDMDAC (polydimethyl diallyl chloride), aluminum sulfate, and CHITOSAN product.

An anti-caking agent may be present in a solid TCMTB formulation of the invention. The anti-caking agents may act as binders, desiccants, or absorbents. These anticaking agents should be slightly hygroscopic to non-hygroscopic in nature and may buffer the uptake of moisture by the solid TCMTB formulation. Granular or powder forms of the anti-caking agents are preferred. The anti-caking agents may be present in amounts up to about 30 percent by weight of the solid formulation, more preferably, from about 1 to about 25 percent by weight, and most preferably from about 5 to about 15 percent. In selecting an anti-caking agent to also act as an absorbent, the anti-caking agent, should preferably be both water-soluble and not promote fungal or bacterial growth. Additionally, when used for its absorbent properties, the anti-caking should be able to convert ample amounts of a liquid TCMTB to a dry powder as contrasted with the formation of a moist mass.

Suitable anti-caking agents are described in Handbook of Pharmaceutical Excipients, 2d Ed., A. Wade and P. Waller, Eds., (Amer. Pharm. Assoc., 1994), which is specifically incorporated by reference in its entirety. Mixtures of anti-caking agents may also be used. Examples of suitable anti-caking agents include, but are not limited to, aluminosilicate (zeolites), magnesium trisilicate, magnesium oxide, magnesium carbonate, magnesium silicate (e.g., magnesium metasilicate, magnesium orthosilicate), calcium carbonate, calcium silicate (e.g., $CaSiO_3$, $CaSiO_4$, $CaSiO_5$), calcium phosphate (e.g., dibasic calcium phosphate, tribasic calcium phosphate), calcium sulfate, talc, fumed silica, zinc oxide, titanium dioxide, attapulgites, activated carbon, silicon dioxide, lactose, microcrystalline cellulose, oxazolidinone and starch.

A suitable silicon dioxide is Hi-Sil 233 which is a white amorphous silica (silicon dioxide) powder having an average diameter of 0.019 microns sold by PPG industries, Inc. The pH of a 5% Hi-Sil 233 solution in water ranges from 6.5–7.3. Other commercial silica products, such as Sipernat 22, 22S can also be used in this application in a similar amount.

Aluminosilicate anti-caking agents include, for example, compounds having the formula $Na_z[(AlO_2)_z(SiO_2)_y]_xH_2O$ where z and y are integers of at least 6, the molar ratio of z to y is in the range from 1.0 to about 0.5, and x is an integer from about 15 to about 264. Useful aluminosilicate ion exchange materials are commercially available. These aluminosilicates can be crystalline or amorphous in structure and can be naturally-occurring aluminosilicates or synthetically derived. See, for example, U.S. Pat. No. 3,985,669, herein incorporated by reference in its entirety. Preferred aluminosilicate anticaking agents include Zeolite A, Zeolite P (B), Zeolite X, Zeolex 23A and Zeolex 7. In an especially preferred embodiment, the anti-caking aluminosilicate is Zeolex 7, a product from J. M. Huber Corporation. Zeolex 7 has an oil absorption of 115 cc/100 g, a pH at 20% of 7.0 and an average particle size of 6 microns. It was determined that Zeolex 7 performed better as an absorbent than Celite 110 (calcined diatomaceous earth from Manville, Denver, Colo.) which has higher oil absorption of 130.

A solid TCMTB formulation according to the invention may also contain a dye or coloring agent as is known in the art. Formulations having different colors may be used to distinguish differences in formulations, for example, different levels of TCMTB, formulations having a certain combination of active ingredients, or formulations for use in a particular aqueous system. Dyes or coloring agents may be incorporated in amounts known in the art, for example from 0 to about 5 percent by weight. Examples of suitable dyes for use in non-oxidizing formulations are Alizarine Light Blue B (C.L. 63010), Carta Blue VP (C.L. 24401), Acid Green 2G (C.L. 42085), Astragon Green D (C.L. 42040), Supranol Cyanine 7B (C.L. 42875), Maxilon Blue 3RL (C.L. Basic Blue 80), acid yellow 23, acid violet 17, a direct violet dye (direct violet 51), Drimarine Blue Z-RL (C.L. Reactive Blue 18), Alizarine Light Blue H-RL (C.L. Acid Blue 182), FD&C Blue No. 1, FD&C Green No. 3 and Acid Blue No. 9. Additional dyes or coloring agents are described U.S. Pat. Nos. 4,310,434 and 4,477,363, and in the Pharmaceutical Excipients, 2d Ed., A. Wade and P. Waller, Eds., Amer. Handbook of Pharm. Assoc., 1994, herein incorporated by reference in its entirety.

When a solid TCMTB formulation is tabletized, the tablet may also include other adjuvants known for use with water treatment tablets. Exemplary adjuvants include, but are not limited to, fillers, binders, glidants, lubricants, antiadherents, water-softening, chelating agents, stabilizers, etc. Examples of such adjuvants, the properties they add to a tablet, and their uses are described in the patents discussed above relating to solid forms of water treatment chemicals. See, for example, U.S. Pat. No. 5,637,308, herein incorporated by reference in its entirety.

A TCMTB tablet formulation of the invention may be formulated for quick disintegration when added to an aqueous system or for sustained release in the aqueous system. Quick disintegration allows for direct dosing of an aqueous system and may be preferable in aqueous systems experiencing problematic microbiological fouling. Sustained release provides a continuous dosing of the system over time. Sustained release tablets may be used for extended prevention or control of biological fouling in an aqueous system such as a swimming pool or a toilet tank. Given the biocidal efficacy of TCMTB both quick disintegration and sustained release tablets can control biofilm or the growth of microorganisms in an aqueous system. The choice between them, as one of ordinary skill appreciates, depends on the particular use.

To control the rate at which a tablet of the invention dissolves in an aqueous system, a disintegration rate regulator (sometimes called a solubility control agent) may be incorporated into the tablet. Disintegration rate regulators are generally hydrophobic materials which retard dissolution of the tablet. In general, any compound which will coat, trap, or otherwise limit the release of the TCMTB or tablet disintegration in the aqueous system to achieve sustained or prolonged release may be used. Some disintegration rate regulators may also beneficially serve as a lubricant or mold release agent during the tableting process.

A disintegration rate regulator, or mixtures thereof, may be present in the tablet in an amount from 0 to about 20 percent by weight of the tablet. More preferably, the disintegration rate regulator is present from about 0.25 to about 10 percent by weight and even more preferably from about 0.5 to about 5 percent. Varying the amount of the disintegration rate regulator affects the rate at which the tablet dissolves in an aqueous system. In general, little or no disintegration rate regulator may be used in quick disintegration tablets while larger amounts may be used in sustained release tablets.

The disintegration rate regulator may be a fatty acid or a derivative of a fatty acid. Fatty acids are composed of a chain of alkyl groups containing from about 4 to about 22 carbon atoms (usually even numbered) and have a terminal carboxylic acid group. Fatty acids may be straight or branched, saturated or unsaturated and even aromatic. Fatty acids generally exist as solids, semisolids, or liquids. In the present invention, the fatty acid or its derivative may act not only as a disintegration rate regulator but also as a lubricant or mold release agent while forming the tablet. Fatty acids and their various derivatives are well-known chemicals and are available from a number of suppliers.

Fatty acids which may be used in the present invention include, but are not limited to, butyric acid, decanoic acid, undecylenic acid, palmitic acid, stearic acid, palmitoleic acid, oleic acid, linoleic acid, linolenic acid, and phenyl stearic acid. The fatty acid derivatives which may be used in the present invention include, for example, fatty acid salts, fatty acid amides, fatty acid alkanolamides, fatty alcohols, fatty amines. Mixtures of fatty acids and/or fatty acid derivatives may also be used. For example, tallow fatty acids, palm oil fatty acids, and coconut oil fatty acids are mixtures of fatty acids useable in the present invention. Derivatives of these fatty acid mixtures may also be used; for example, amide derivatives such as dimethyl amide derivatives of tall oil (DMATO) or palm oil (DMAPO).

One group of preferred disintegration rate regulators are those related to stearic acid. These include but are not limited to stearic acid, potassium stearate, magnesium stearate, polyoxyethylene stearate/distearates, polyoxyethylene-2 stearyl ether, glyceryl monostearate, hexaglyceryl distearate, glyceryl palmitostearate, and sodium stearyl fumarate. Magnesium stearate is particularly preferred and is available from Witco Corporation and Mallinkrodt Specialty Chemical Co. The polyoxyethylene stearates/distearates are a series of polyethoxylated derivatives of stearic acid available from ICI Americas, Inc., Wilmington, Del. These include, for example, polyoxyl 6 stearate, polyoxyl 8 stearate, polyoxyl 12 stearate, polyoxyl 20 stearate, polyoxyl 40 stearate, and polyoxyl 50 stearate. Glyceryl monostearate is available from Ashland Chemical Co., Columbus, Ohio. Glyceryl palmitostearate is available from Abatar Corporation, Hickory Hills, N.J. A stearic acid based product having a mixture of compounds is STE-ROWET product, a mixture of calcium stearate and sodium lauryl sulphate.

Polyoxyethylene sorbitan esters or polysorbate esters, represent another group of preferred disintegration rate regulators. These polysorbate esters are sold under as "TWEEN" products available from ICI Americas Inc., Wilmington, Del. Exemplary esters include polysorbate 81 (TWEEN 81 Product), polysorbate 85 (TWEEN 85 Product), polysorbate 61 (TWEEN 61 Product), polysorbate 65 (TWEEN 65 Product), and polysorbate 21 (TWEEN 21 Product).

Polyoxyethylene ethers, preferably those having alkyl chains of about ten carbons or more, may also be used as disintegration rate regulators in tablets of the invention. These longer alkyl chains increase the hydrophobicity of the ether. Polyoxyethylene ethers are available from ICI Americas Inc., Wilmington, Del. Examples of these ethers include 2 cetyl ether, 2 stearyl ether, 3 decyl ether, 3 lauryl ether, 3 myristyl ether, 3 cetyl ether, 3 stearyl ether, 4 lauryl ether, 4 myristyl ether, 4 cetyl ether, 4 stearyl ether, 5 decyl ether, 5 lauryl ether, 5 myristyl ether, 5 cetyl ether, 5 stearyl ether, 6 decyl ether, 6 stearyl ether, 7 lauryl ether, 7 myristyl ether, 7 cetyl ether, 7 stearyl ether, 8 lauryl ether, 8 myristyl ether, 8 cetyl ether, 8 stearyl ether, 9 lauryl ether, 10 lauryl ether, 10 tridecyl ether, 10 cetyl ether, 10 stearyl ether, 10 oleyl ether, 20 cetyl ether, 20 isohexadecyl ether, 20 stearyl ether, 20 oleyl ether, and 21 stearyl ether.

Other disintegration rate regulators which may be used include hydrogenated vegetable oils such as the STEROTEX product and Durotex product from Capital City Products of Columbus Ohio. The disintegration rate regulator may also be a wax such as carnauba wax, petroleum ceresin (available from International Wax Refining Co., beeswax (yellow wax) or shellac, (the latter two, available from Van Waters and Rogers). Aliphatic amides such as cocoa amide and octadecanoic amide or hydrogenated tallow amides such as oliamide may also be employed as disintegration rate regulators. Polyethylene amides may also be included in a tablet as a disintegration rate regulator.

A particular disintegration rate regulator may be chosen for use in a tablet on the basis of its properties, for example, ease of use in the tableting process and benefits to the final tablet. The disintegration rate regulator of choice may be slightly, moderately, or very hydrophobic depending upon the particular use. Less hydrophobic regulators are generally used for quick disintegration tablets and more hydrophobic ones for sustained release tablets. For example, sodium stearyl fumarate is less hydrophobic than either stearic acid or magnesium stearate. Thus, sodium stearyl fumarate may be used to increase the rate of dissolution over tablets containing stearic acid or magnesium stearate. Mixtures of disintegration rate regulators may be used to a achieve a desired degree of hydrophobicity or rate of dissolution.

A tablet TCMTB formulation may be coated with coatings known in the art. For example, a tablet of the invention may be provided with a coating of a water-soluble film, such as polyvinyl alcohol, to make handling more convenient.

Recent advances in coating technology, such as side vented pans, have increased the efficiency of aqueous coating operations. Among the most common ways to apply coatings is through film coating (deposition of a coat through an aqueous or solvent base) or compression coating (compressing a coating around a core tablet). Techniques such as these could also permit the addition of agents to the surface of tablet imparting additional sustained characteristics to the tablets. Somewhat analogous to coatings, the tablet may be manufactured as an inlay tablet or multilayered tablet in which the TCMTB-containing portion is "sandwiched" between, for example, slow release matrices. This may also create a sustained release tablet according to the invention. For additional reference consult "Pharmaceutical Dosage Forms: Tablets Vols. 1–3", 2d Ed., 1989, H. A. Lieberman, L. Lachman, and J. B. Schwartz, Eds, herein incorporated by reference in its entirety.

Method of Making a Powder TCMTB Formulation

A solid TCMTB formulation can be made by combining a solution of TCMTB with a water-soluble, salt carrier matrix to form a powder. In general, a solution of TCMTB is sprayed onto, or mixed with, the salt carrier matrix, or a solid preblend of the salt carrier matrix and other solid components, to form a solid TCMTB formulation. For example, a solid microbicide may be mixed with the salt carrier matrix to form a preblend prior to combining the preblend with the TCMTB solution. Additionally, the TCMTB solution may also contain soluble components to be incorporated into the solid TCMTB formulation. To avoid agglomeration, the TCMTB solution should be applied to the salt carrier matrix or solid preblend in the substantial absence of high shear and without excessive heat. This may be accomplished by spraying a TCMTB solution onto a salt carrier matrix or solid preblend while keeping the salt carrier matrix or solid preblend in motion. This method, combining a TCMTB solution with a salt carrier matrix, may be used to form solid TCMTB powder formulations having a variety of particle sizes ranging from dusts to particulates and even granules. The particle size generally depends upon the initial particle size of the salt carrier matrix or the solid preblend. Milling or grinding steps may be used if desired to further reduce the particle size after forming the solid TCMTB formulation. The particle size of the solid TCMTB powder formulations generally depends upon the particle size of the salt carrier matrix. In the preferred solid TCMTB formulation, substantially all of the powder in the solid TCMTB formulation has a particle size of less than 100 microns. Preferably, more than 80% of the powder has a particle size of less than 20 microns.

In preparing a solid TCMTB formulation according to the invention, it may be necessary to process the salt carrier matrix before combining it with a solution of TCMTB. For example, a salt carrier or carriers, as well as any other solid components, may be mixed in a blender such as a Ribbon blender to achieve the desired size and ratio of particles, especially if more than one type or size of salt carrier or solid component is used. By mixing in the solids in a blender, a preferred uniform particle size may be obtained for the carrier powder formulation. Uniform particle size allows even distribution of components and consistent dispersion of active ingredient, particularly in an aqueous system.

After forming the salt carrier matrix or a solid preblend, a liquid TCMTB mixture which contains the TCMTB and any other liquid component is combined or mixed with the salt carrier matrix formed in the first step. This may be accomplished in a blender or a suitable powder coating apparatus which can be preferably used to apply, such as by spraying, the liquid TCMTB mixture, onto the salt carrier matrix or solid preblend. The liquid TCMTB mixture is combined with the carrier powder or solid preblend until the two components form a powder preferably with the TCMTB completely adsorbed onto the carrier powder. If necessary, the powder may be granulated to form a flowable solid TCMTB powder formulation of a desired size. The powder formed by the invention is preferably a free flowing, low dusting, particulate like product having a consistent and uniform size and formulation.

To apply TCMTB to a salt carrier matrix or solid preblend, the TCMTB is dissolved or dispersed in a solvent. Other components for the solid TCMTB may also be dissolved or dispersed in the solvent. This is preferable for components, such as emulsifiers, which may not be easily mixed with the salt carrier matrix to form a solid preblend or which are in liquid form. If needed a mixture of solvents, including water, may be used to incorporate all desired components into the TCMTB solution before application to the solid carrier. Preferably, the solvent should possess one or more of the following characteristics: (1) high solvency for TCMTB, (2) low volatility, (3) non-flammability, (4) high flash point, (5) low phytotoxicity, (6) low viscosity, (7) availability, (8) low cost, (9) low odor and (10) absence from regulatory lists of hazardous substances; e.g., SARA 313 and CERCLA.

In a solid TCMTB formulation of the invention, the amount of solvent, if used in making the solid formulation, preferably is not greater than 10% by weight of the formulation. If a solvent is used, the solvent can be any TCMTB compatible solvent, such as:

(1) oxygenated solvents: diethylene glycol monoethylether, diethylene glycol monomethylether, diethylene glycol monobutylether, hexylene glycol, alkyl acetate, such as EXXATE™ 600, 700, 800, 900, 1000 or 1300 product, isophorone and propylene glycol;

(2) amide products from the reaction of tall oil, soy oil, palm oil, coconut oil, cotton seed oil, sunflower oil, safflower oil, and peanut oil with dimethylamine;

(3) aromatics (xylenes, alkylbenzene derivative);

(4) aliphatics and paraffinics; mineral oil, mineral soil oil;

(5) cycloparaffin;

(6) animal or vegetable oils;

(7) esters: methyl oleate, butyl oleate, glyceryl oleate, methyl tallowate, methyl soyate;

(8) miscellaneous: oleic acid, tetrahydrofurfuryl alcohol, dimethyl formamide, alkyl alcohol, such as Texanol™ alcohol, and N-methyl 2-pyrrollidone; and (9) mixtures of any two or more of the above-mentioned solvents.

Particularly preferred solvents include dipropyleneglycol monomethylether, mineral oil, tetrahydrofurfuryl alcohol and natural oils such as Castor oil, since these solvents possess the desirable characteristics noted above.

The method may be carried out in a P-K blender, a Turbulizer, a fluid bed sprayer or Wurster coating apparatus. A P-K blender may be used to accomplish both the mixing of the salt carrier matrix and/or the combining of the TCMTB solution with the salt carrier matrix. A P-K blender is manufactured by the Paterson-Kelley of East Stroudsburg, Pa. The P-K blender used in the invention preferably has the ability to mix the materials homogeneously, disperse the liquid evenly across the solid, remove solvents from the mixture and grind the final product to the proper particle size and consistency. Also, the P-K blender preferably has high speed choppers which supplement the blending action of the plows. These high speed choppers can enhance the basic mixing action, quickly disperse minor ingredients, and reduce/eliminate the need to premill the solid components to the desired powdered sizes.

Alternatively, a Turbulizer™ apparatus or a Turbulator™ apparatus can be used as the powder coating apparatus. The Turbulizer™ apparatus is manufactured by the Bepex Corporation of Minneapolis, Minn. The use of the Turbulizer™ apparatus is described in more detail in U.S. Pat. No. 5,043,090, the disclosure of which is incorporated herein by reference in its entirety. The Turbulator™ apparatus is manufactured by Ferro-Tech of Wyandotte, Mich. A preferred paddle setting of Turbulizer™ apparatus can be: four forward, five flat, and one backward. The rotor speed can be set at various speeds, including 1800 rpm. The Turbulizer™ apparatus can be operated at room temperature without a cooling jacket. If desired, further processing can be conducted in the Turbulizer™ apparatus at a high rotor speed (3600 rpm) to reduce the powder size, i.e., de-agglomerate, the powder.

According to the invention, one can obtain a substantially homogeneous TCMTB powder formulation, i.e., the TCMTB is absorbed evenly onto the water-soluble salt carrier matrix. If a reduction in particle size is desired, a hammer mill or pulverizer can also be utilized. Depending upon the particle size desired, the pulverizer can be utilized with a one-to-three beater with $\frac{1}{16}$ inch plate with mill speed up to 7200 rpm with the classifier set at 4500 rpm or higher. One skilled in the art can routinely select mixing items and settings to achieve desired results, such as homogeneity of the solid TCMTB formulation of the invention.

In a preferred method of making a solid TCMTB powder formulation, the solid components, including the salt carrier matrix, are blended in a P-K Twin Shell Blender with the liquid components, including the TCMTB. No heating or cooling is required. This operation preferably occurs under a slight vacuum, which assists in removing excess water or any solvent which is liberated from the TCMTB solution. The product formed in the P-K Twins Shell Blender is discharged under a vacuum into intermediate storage until all batches are completed.

The particle size of a solid TCMTB powder formulation generally depends upon the particle size of the salt carrier matrix. In the preferred solid TCMTB powder formulations, substantially all of the powder in the solid TCMTB powder formulation has a particle size of less than 100 microns. Preferably, more than 80% of the powder has a particle size of less than 20 microns.

Tabletizing

In another embodiment, the solid TCMTB formulation of the invention may be formed into tablets. "Tablet" forms include tablets themselves as well as other solid forms or shapes known in the art such as sticks, pucks, briquets, pellets and the like. Any shape of tablet may be used. Tablets may be prepared by compressing a solid TCMTB powder formulation described above. The particle size of the powder may vary and generally depends upon the size of the tablet to be formed. Larger tablets do not require as small a particle size as smaller tablets. The powder used for forming a tablet preferably has a particle size of less than 12 mesh and may be about 200 to about 400 mesh or smaller.

The size of a tablet according to the invention may vary depending upon its intended use. For example, water treatment tablets used to treat a swimming pool or a cooling tower may be approximately 200 to 400 grams. As one of ordinary skill knows, the tablet size depends to some extent on the size and needs of the particular system.

Before compressing the solid TCMTB powder formulation into a tablet, other tabletizing components such as those discussed above may be added to the solid TCMTB powder formulation in an optional blending step, preferably a dry blending step. Thus, for example, the solid TCMTB powder formulation may be blended with for example, a disintegration rate regulator, an anticaking agent, a dye and/or other tabletizing components. Additional grinding and/or screening may also be done after blending, if desired or necessary. If liquid formulations are added at this stage, additional drying, grinding and/or screening steps may also be used.

"Compressing" the powder into a tablet may be accomplished using tablet formation procedures known in the art. Preferably, the powdered TCMTB is compressed into a tablet using pressure. Tableting pressures generally range from about 10 to about 40 tons per square inch.

The amount of pressure applied to compress the powder into a tablet should not be too low such that the resulting tablet is weak and without integrity, or for sustained release applications, dissolves too rapidly. If the pressure is too high, the tablet may dissolve too slowly. The actual pressure employed for making a tablet out of any particular powder will depend, to some extent, upon the tablet's end use (quick disintegration or sustained release), its components and their relative proportions in the mixture. In any event, it will be a routine matter to establish the preferred method and/or pressure for tableting solid TCMTB powder formulations according to the invention.

Packaging the Solid TCMTB Formulation

When using a solid TCMTB formulation of the invention it is preferable to avoid direct user contact. To reduce or even eliminate direct user contact, a TCMTB solid formulation may be contained in a water-soluble container. Preferably the water-soluble container is a sealed water-soluble bag. The amount of solid TCMTB formulation contained in a water-soluble container may generally depends the amount of TCMTB and/or other active ingredient in the formulation and its intended use. However, a typical water-soluble bag has a minimum capacity of about 100 grams to 900 grams for reasons of convenience.

Packaging the solid TCMTB formulations in water-soluble containers not only reduces handling exposure but allows convenient sizing for a variety of commercial and industrial cooling water systems, leather tanning operators, and wood treatment preservative appliers, such as discussed above. By packaging the solid TCMTB in convenient sizes for controlled dosages, a user may add the solid TCMTB to an aqueous system without coming directly into contact with the solid TCMTB formulation itself Because the container is itself water-soluble, its integrity should be preserved by reducing its exposure to excess humidity and moisture. This may be accomplished by packaging the containers in a protective moisture proof outerwrap.

A water-soluble container can be manufactured from a number of water-soluble films which are available commercially. Suitable water-soluble, film-forming materials are discussed in Dunlop et al. U.S. Pat. No. 3,198,740 and Gladfelter et al. U.S. Pat. No. 5,235,615 which are incorporated by reference in their entirety. Water-soluble film forming materials suitable for the invention include, but are not limited to, the following: polyvinyl alcohol, polyvinyl acetate, methyl cellulose, hydroxyethyl cellulose, carboxymethyl cellulose, sodium carboxymethylhydroxyethyl cellulose, polyvinyl pyrrolidone, poly(alkyl)oxazoline, and film-forming derivatives of polyethylene glycol.

A preferred water-soluble polymer is polyvinyl alcohol which is an excellent film forming material. Films formed from polyvinyl alcohol exhibit strength and pliability under most conditions. Commercially available polyvinyl alcohol formulations for casting as films vary in molecular weight and degree of hydrolysis. For most film applications, molecular weights ranging from about 10,000 to about 100,000 are preferred. Hydrolysis is the percent by which acetate groups of the polyvinyl alcohol have been substituted with hydroxyl groups. For film applications, the range of hydrolysis typically is about 70% up to 100%. Thus, the term "polyvinyl alcohol" usually includes polyvinyl acetate compounds. Polyvinyl alcohol film can be hygroscopic and its physical properties can change with changes in temperature and humidity. Thus the sealed water-soluble container containing the solid TCMTB formulation should be protected from atmospheric humidity.

Water-soluble films, and the water-soluble bags manufactured from them, are available from a number of commercial sources including the MONO-SOL Registered TM Division of Chris Craft Industries, Inc. A particularly useful type of a water-soluble polyvinyl alcohol film is the 7-000 series of polyvinyl alcohol films which is available from the MONO-SOL Registered TM Division of Chris Craft Industries, Inc. The 7-000 series of polyvinyl alcohol films dissolve at a water temperature of about 1° C.–95° C. Such films are nontoxic and display a high degree of chemical resistance. A 0.002 inch+/–0.0002 inch thick 7-000 series polyvinyl alcohol film has the properties and performance characteristics shown in Table 1:

TABLE 1

| Properties | Value | Test Method |
| --- | --- | --- |
| Clarity | Translucent | |
| Yield (in./lb.) | 11,600 in./lb. | |
| Hot bar heat seal range | 150–175° C., 30 psi, 3/4 | |
| Impulse heat seal range | 0.8–1.0 second, 80 psi, | |
| Water temperature range for solubility | 1° C.–95° C. | |
| Performance | Value | |
| Tensile strength (at break) | 6000 lb./sq. in. minimum | ASTM D822 |
| Tear strength | 1000 gm/mil. in. minimum | ASTM D1922 |
| Burst strength (Mullen) | Exceeds limit of equipment | TAPPI |
| Elongation | 450% min. | ASTM D822 |

When selecting a water-soluble film for use in the water-soluble container, one should take into account the water temperature at which the water-soluble container is expected to dissolve. It is desirable to choose a water-soluble film that can dissolve at a low water temperature so that the invention functions properly over a wide range of water temperatures. Useful water-soluble films for use in the water-soluble containers include those that dissolve at a water temperature of as low as about 1° C.

It is also important to select a water-soluble film that does not react with the solid TCMTB formulation contained in the water-soluble container. Other factors which should be considered when choosing a water-soluble film to form the water-soluble container include the following: the effect of the water-soluble film on equipment including pumps, pipes and nozzles; the effect of the water-soluble film on waste water; the toxicity of the water-soluble film; the printability of the water-soluble film; and properties which allow the water-soluble film to be used on automated bag-making equipment (i.e., sealability, tensile strength and tear strength). Printability is a factor since one may desire to print appropriate warnings and instructions on the water-soluble container.

Materials useful as the water-soluble container should have the following minimum properties in order to be successfully utilized. The material should have a maximum hot bar heat seal range of about 175° C. The material should have a minimum water temperature range for solubility of about 1° C. The material should have a minimum tensile strength (at break) of about 6000 lb./sq. in. according to the ASTM D822 test method. The material should have a minimum tear strength of about 1000 gm/mil according to the ASTM D1922 test method. The material should have a minimum elongation of about 450% according to the ASTM D822 test method.

A water-soluble container of the invention may be of whatever dimensions necessary in order to enclose the desired amount of the solid TCMTB formulation. A water-soluble container can be made according to the general methods employed by the plastic film package producing industry.

The preferred water-soluble bag of the invention may be prepared from the water-soluble film by placing two rectangular sheets of the water-soluble film face-to-face so that the edges coincide and heat sealing or water sealing three edges using sealing equipment and methods known in the industry. After sealing three edges, the water-soluble bag is filled by pouring the weighed solid TCMTB formulation and finally heat sealing the fourth edge. The thickness of a wall of the water-soluble bag can range from about 20 to 90 microns, preferably about 25 to 50 microns for reasons of solubility, and most preferably about 50 microns for reasons of effective containment, rapid solubility and machinability. Typically, the length of a water-soluble bag may range from about 6 to 18 inches, preferably about 8 to 16 inches, for reasons of automated filling and most preferably about 10 to 14 inches, for reasons of fit within the dispenser. The width of the water-soluble bag can range from about 5 to 10 inches, preferably about 6½ to 8 inches for reasons of automated filling, and most preferably about 7 to 7½ inches. The water-soluble bag should preferably have a dissolution rate ranging from about 0.5 to 30 minutes at a water temperature of about 5° C. to 85° C. and a water pressure of about 25–30 psig.

As discussed above, in order to protect the water-soluble container from atmospheric humidity during storage, shipping and handling, a water impervious outerwrap can be provided. For example, a re-sealable zip-lock outerwrap may be used. The outerwrap helps prevent damage from atmospheric moisture such as high humidity, rain and dew and from accidental contact with water by splashing or wet hands. This water impervious outerwrap can be provided for either an individual water-soluble bag or a group of bags, whichever appears to be most desirable for the individual case. Preferably, the water impervious outerwrap is provided individually for each bag for reasons of customer safety and convenience and product protection. Once the water impervious outerwrap is removed, the water-soluble container should be protected from water contact or placed into the aqueous system. Additionally, a water impervious outerwrap can be used to protect the water soluble bag from exposure to light.

The water impervious outerwrap can comprise a variety of forms including but not limited to the following: a box, a carton, an envelope, a bag, a tub, a pail, a can and a jar. Preferably the water impervious outerwrap comprises a flexible bag for reasons of ease of handling and storage.

Suitable materials for the water impervious outerwrap include but are not limited to the following: polyolefin films such as polyethylene or polypropylene, Kraft paper which can be moisture-proofed with polyethylene, moisture proofed cellophane, glassine, metal foils, metallized polymer films, mylar, polyester, polyvinyl chloride, polyvinylidene chloride or waxed paper and combinations of these materials as in laminates. The selection of material for the water impervious outerwrap is determined by a number of factors including the cost of the material and the strength required. Preferably, the water impervious outerwrap comprises a polyethylene film for reasons of cost of material and moisture barrier properties.

A preferred polyethylene film available from several manufacturers for use in the production of the water impervious outerwrap has the following properties:

| Structure | |
| --- | --- |
| Antistatic coating | |
| High density polyethylene | 20% |
| White linear low density polyethylene | 60% |
| Surlyn (sealant layer) | 20% |
| Caliper: absolute minimum thickness 2.70 mil. inch | |
| * | Value |
| Properties | |
| Clarity (% light transmission) | 34.4% |
| Yield (sq. in./lb.) | 10,561 |
| Heat seal range | 90–120° C., 60 psi, |
| * | ½ second dwell |
| Water vapor transmission rate | 0.18 |
| WVTR (gm/100 sq. in./24 hours at 38° C., 90% R.H.) | |
| Oxygen transmission test | 95.0 |
| O₂ trans (cc/100 sq. in. 24 hours/1 atm./23° C., 50% R.H.) | |
| Performance Properties | |
| Tensile strength (at break) | 3300 min.–3900 max. psi |
| Tear strength | 616 g MD/536G MD |
| Elongation | 663% MD/620% CD |
| Dart impact (50% failure) | 214G |

Materials useful as the water impervious outerwrap should preferably have certain minimum properties in order to be successfully utilized as the water impervious outerwrap. Preferably, the outerwrap material has a water vapor transmission rate (WVTR) of no more than about 0.5 gm/100 sq./24 hours at about 40° C., 90% R.H.; minimum tensile strength (at break) of about 3000 psi.; a minimum wall thickness of about 35 microns; and a minimum capacity of about 100 grams.

Bags to serve as the moisture impervious outerwrap are made by methods known in the art similar as with the water-soluble film bags; heat sealing three edges except that the films are typically cut to be about 1 to 3 inches wider and about 1 to 4 inches longer than the water-soluble bag which it contains. A margin of the moisture impervious outerwrap, preferably the side margin, can contain a slit which extends part way through the margin to aid the user in opening the moisture impervious outerwrap. The fourth side is preferably sealed by means known in art, such as a zip lock or by heat in order to provide at least about a 10 mm margin.

Methods of Using Solid TCMTB Formulations

A solid TCMTB formulation of the invention may be applied in a variety of industrial uses and processes for microorganism control. The formulation may be used in place of and in the same manner as other microbicide formulations traditionally used in the particular industry. As discussed above, such industries include, but are not limited to the leather industry, the lumber industry, the papermaking industry, the textile industry, the agricultural industry, and the coating industry. The solid TCMTB formulation may also be used with aqueous systems such as those previously discussed which are subject to microbiological attack and degradation. The problems caused by microbiological attack and deterioration in these various applications has been described above. The use of the solid TCMTB formulation according to the invention to control the growth of microorganisms in particular exemplary applications is described below.

The invention relates to a method for controlling the growth of at least one microorganism on various substrates and in various fluid systems. The method comprises the step of treating a substrate or a fluid susceptible to microbiological growth or attack with a solid TCMTB formulation, as described above. The TCMTB is present in an amount effective to control the growth of at least one microorganism on the substrate or in the fluid. As stated above, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time.

Typically, the solid TCMTB formulation is added to a solvent to form a liquid TCMTB formulation. Preferably the solvent is water. This liquid formulation is then contacted with the substrate or fluid system for which microorganism control is desired. Generally the fluid system to be treated is an aqueous system. By controlling the growth of at least one microorganism in an aqueous system, the aqueous system is protected from biological degradation as well as the surfaces and substrates in contact with the aqueous system. Preferred applications of this general method are discussed below.

In one embodiment, a solid TCMTB formulation may be used in the leather industry to control the growth of microorganisms on a hide during a tanning process. To achieve this control, the hide is contacted with an amount of TCMTB effective to control the growth of at least one microorganism on the hide. A solid TCMTB formulation may be used in the tanning process in similar amounts and manner similar to that used to apply other microbicides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fat liquoring stage. A solid TCMTB formulation may be used during all process stages in the tanning process in addition to those stages where a known microbiological problem is occurring. In each stage, a solid TCMTB formulation may be added to the appropriate tanning liquor applied to the hide undergoing tanning.

Adding a solid TCMTB formulation in a tanning liquor protects the hide from microbiological deterioration during the tanning process. Preferably, the formulation is uniformly dispersed, e.g., under agitation, into an appropriate liquor to be used in a tanning process or added to an appropriate liquor in an on-going tanning process. Typical tanning liquors include, for example, a pickling liquor, a chrome-tanning liquor, a vegetable-tanning liquor, a post-tan washing liquor, a retanning liquor, a dye liquor, and a fat liquor. This method of application protects the hides against microbiological attack, deterioration, or other microbiological degradation.

Generally, to prevent bacterial growth on brine-cured hides and skins the solid TCMTB formulation may be used at a level of about 225–1150 grams per 1000 lbs of green fleshed hides or skins. A solid TCMTB formulation is preferably added prior to or immediately after the hides to the raceway. To assure adequate mixing, the bags and/or tablets may be individually introduced to the input side of the raceway paddle. Additionally, a solid TCMTB formulation can be used to prevent bacterial degradation of hides and skins during the soaking process. A solid TCMTB formulation may be used at a level of about 450 to 900 grams per 450 kilograms of green or brine fleshed hides or skins. Also, a TCMTB can be used to prevent mold growth on chrome or vegetable-tanned hides or skins during tanning or post tanning operations prior to finishing. A solid TCMTB formulation may be used at treatment rates of about 225 grams to 1360 grams per 450 kilograms of white weight stock. Individual bags or tablets of solid TCMTB or can be added directly to the tanning drum or vessel or dissolved in a chemical mix box during the tanning process.

In a somewhat analogous nature, a solid TCMTB formulation of the invention may also be employed to control the growth of microorganisms on a textile substrate in a textile manufacturing process. Contacting the textile substrate with TCMTB according to the invention effectively controls the growth of a microorganism on the textile substrate. In a textile process, the combination may be used in similar amounts and a manner similar to other microbicides commonly used in such processes. As one of ordinary skill would appreciate, particular amounts generally depend on the textile substrate and the degree of microbiological resistance required.

To control microbiological growth, a textile process generally dips the textile substrate into a bath containing a microbicide, alone or with other chemicals used to treat the textile substrate. Alternatively, the textile substrate may be sprayed with a formulation containing a microbicide. A solid TCMTB formulation according to the invention may be added directly to the bath or spray prior to or during use. In the bath or the spray, a solid TCMTB formulation according to the invention is added such that the TCMTB is present in an amount effective to control the growth of at least one microorganism on the textile substrate. Preferably, the bath and the spray are aqueous-based formulations.

To preserve the value of its raw materials and products, the lumber industry also must control the growth of microorganisms in order to prevent microbiological degradation. A solid TCMTB formulation according to the invention is effective for controlling the growth of microorganisms on lumber. Typically, a solid TCMTB formulation may be used to protect the lumber in similar amounts and a similar manner employed for other microbicides used in the lumber industry. For example, a solid TCMTB formulation may be used to control sapstain and mold on freshly cut hardwood and softwood lumber, logs, poles, posts and timbers. Contacting lumber with an effective amount of the TCMTB may be accomplished by spraying the lumber with an aqueous formulation containing a solid TCMTB formulation, and by dipping the lumber into a dip bath containing the formulation. Dipping the lumber in an aqueous bath is preferred. Preferably, a solid TCMTB formulation is uniformly dispersed in a bath (for example, by agitation) prior to the dipping of the lumber into the bath or during an on-going process. Generally, about 6 to 24–450 gram bags of solid TCMTB formulation are added per 100 gallons of water. This mixture is agitated vigorously until a solid TCMTB formulation is thoroughly dispersed. Rates to be used will vary according to temperature, humidity, wood moisture, storage conditions, etc. Under conditions suitable for aggressive mold growth, the high rate mentioned above should be used. Treatment should be made as quickly as possible after lumber is cut and always within 24 hours after cutting.

In general, the lumber is dipped into the bath, raised, allowed to drip dry, and then air dried. The dip time will depend, as is known in the art, on a variety of factors such as the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath.

A solid TCMTB formulation according to the invention also has uses in the agricultural industry. To control the growth of microorganisms on an agricultural product, such as a seed or plant, the seed or plant may be contacted with TCMTB in an amount effective to control the growth of at least one microorganism on the seed or plant. This contacting step may be accomplished using amounts known in the agricultural industry for other microbicides. For example, the seed or plant may be sprayed with an aqueous formulation containing a solid TCMTB formulation or dipped into a bath containing the formulation. After being sprayed or dipped, the seed or plant is generally dried by means known in the art such as drip drying, heated drying, or air drying. For plants or crops, the TCMTB may also be applied using a soil drench. Soil drenching is particularly advantageous when the microorganisms of concern inhabit the soil surrounding the plant.

Yet another aspect of the present invention is a method for controlling the growth of microorganisms in an aqueous system capable of supporting such growth. The aqueous system is treated with a solid TCMTB formulation such that the TCMTB is present in an amount effective to control the growth of at least one microorganism in the aqueous system. This includes controlling, and preferably preventing, slime formation in the aqueous system.

Examples of various aqueous systems include, but are not limited to, oil field waters, latexes, surfactants, dispersants, stabilizers, thickeners, adhesives, starches, waxes, proteins, emulsifying agents, cellulose products, aqueous emulsions, aqueous detergents, coating formulations, paint formulations, alum formulations, and resins formulated in aqueous solutions, emulsions or suspensions. A solid TCMTB formulation may also be employed in aqueous systems used in industrial processes such as metal working fluids, cooling waters (both intake cooling water and effluent cooling water), and waste waters including waste waters or sanitation waters undergoing treatment of the waste in the water, e.g. sewage treatment.

As mentioned above, a solid TCMTB formulation may be used to control algae, bacteria and fungi in industrial recirculating water systems, such as a cooling water system or metal working fluid. A solid TCMTB formulation may be added to an existing recirculating water system. When treating a recirculating water system, the system should preferably be cleaned thoroughly prior to adding the TCMTB in order to remove old algal growth, microbiological slime, and other deposits. The system should then be drained, flushed, refilled with water, and treated with an initial dose of about 1 to 2–100 gram bag(s) of solid TCMTB formulation per 1000 gallons water in the system. A subsequent addition of about 1–100 gram bag of solid TCMTB formulation per 1000 gallons may be made every 1 to 5 days, depending on amount of system bleed off and the severity of microbiological fouling.

To inhibit bacterial and fungal degradation of the fluids or muds used in the drilling of wells, a solid TCMTB formulation is incorporated in the drilling fluid at concentrations of about 4 to 24–450 gram bags of Busan 1350 per 1000 gallons of fluid.

As disclosed above, a solid TCMTB formulation may be used to control sulfate-reducing bacteria, slime-forming bacteria and fungi in oil-field water, polymer, or micellar floods, water-disposal systems, and other oil-field water systems. Typically, the dosage rates of solid TCMTB formulations range from about 1 to 4–100 gram bag(s) per 1000 gallons of water treated. Additions should be made continuously or intermittently by means of a metering pump at the free water knockouts, before or after injection pumps and injection well headers. Alternatively, an intermittent or slug method of treatment may be used when system is noticeably fouled, or to maintain control. For such an intermittent or slug method about 1 to 4–100 gram bag(s) of solid TCMTB formulation are added per 1000 gallons of water, 1 to 4 times per week, or as needed to maintain control.

A solid TCMTB formulation may also be used as an oil-soluble preservative for the control of bacteria and fungi that cause the degradation of crude oil and refined oils during storage. Crude and refined oils include, but are not limited to, olefinic, aromatic, paraffinic, and naphthionic oils. A solid TCMTB formulation may be added to the oil as it is being transferred from the shipping container to the storage tank at the rate of about 1 to 2–100 gram bag(s) of solid TCMTB formulation per 1000 gallons of oil. Addition should be made batchwise where mixing occurs.

As with the other uses discussed above, a solid TCMTB formulation of the invention may be used in the same amounts and in the same manner as microbicides traditionally used in these various aqueous systems. The formulation not only protects the aqueous system prior to use or when stored, but in many cases protects the aqueous system when in use or in appropriate applications even after the aqueous system has dried. When used in a paint formulation for example, the formulation not only protects the paint in the can, but also the paint film after being applied to a substrate.

Another embodiment of the present invention is a method for controlling the growth of microorganisms on paper or in a papermaking process, e.g., in a pulp or paper slurry and on a finished paper product such as paper board. The paper, pulp, or slurry is contacted with a solid TCMTB formulation in an amount effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with TCMTB by spraying an aqueous dispersion containing a solid TCMTB formulation onto the pulp after the pulp leaves the presses in a papermaking process. Alternatively, a solid TCMTB formulation may be added directly into a bath used at the wet or size press and the web contacted by nipping the web to incorporate the TCMTB into the web with any other agents applied at the press. Furthermore, the pulp may be contacted by adding a solid TCMTB formulation directly to the pulp/white water mixture, preferably prior to the pulp reaching the formation wire.

When treating paper (which includes paperboard and other cellulosic products or substrates), a solid TCMTB formulation may be added into pulp slurries in the headbox, in the substrate forming solution, or in the white water system to treat the water system itself or for incorporation into the body of the paper. Alternatively, as with other known microbicides, a solid TCMTB formulation according to the invention may be mixed into a coating used to coat the finished paper.

EXAMPLES

Example 1

A solid TCMTB powder formulation of the invention was produced by mixing the following components in a V-blender (P-K blender):

| Ingredients | Wt % (final formula) |
|---|---|
| TCMTB-60 | 13.34% |
| Tergitol XD | 1.00% |
| Casul 70 HF | 0.15% |
| Sodium Sulphate, anhy. | 64.30% |
| Hi-Sil 233 | 2.00% |
| Stepwet DF-90 | 1.00% |
| Zeolox 7 | 10.00% |
| MTC (methylene bisthiocyanate) | 8.20% |

TCMTB-60 contains TCMTB and dipropylene glycol monomethyl ether.

Tergitol XD is a block copolymer of ethyleneoxide and propyleneoxide reacted with butanol.

Casul 70 HF is calcium dodecylbenzene sulfonate in butanol solvent.

Hi-Sil 233 is a white amorphous silica (silicon dioxide) powder.

Stepwet DF 90 is a product from Stepan company, Northfield, Ill. The generic name is sodium dodecylbenzene sulfonate.

Zeolex 7 is a product from J. M. Huber Corporation, Havre de Grace, MD. The generic name is sodium aluminosilicate.

The solid TCMTB powder formulation was formed by chopping, in a PK-blender, a solid rock-like MTC into a powder. To the MTC powder were added the other solid components including anhydrous sodium sulphate, Hi-Sil 233 and Zeolox 7 to form a salt carrier matrix preblend. Separately, the liquid TCMTB was mixed with the other liquid components, Tergitol XD, Casul 70 HF and Stepwet DF-90 to form a liquid TCMTB mixture. This liquid TCMTB mixture was then added to the salt carrier matrix preblend contained in the PK-blender. The liquid and solid components were mixed together for about 50 minutes to form a powder. To ensure the proper consistency of the powder, the resulting powder mixture chopped was for 30 seconds and then allowed to sit for 30 seconds. This chopping process was repeated for as many times necessary to achieve the desired powdered product.

Example 2

The following solid TCMTB tablet formulation were produced by using a V-blender (P-K blender):

| Ingredients | Wt % (final formula) |
|---|---|
| TCMTB solution | 13.7% |
| MTC | 10.4% |
| Sodium Sulphate, anhy. | 62.9% |
| Hi-Sil 233 (silica) | 0.5% |
| Stearic acid | 0.5% |
| Stepwet DF-90 | 1.00% |
| Zeolox 7 | 10.00% |

The TCMTB solution contained 92% TCMTB-80, 7% Tergitol XD, and 1% Casul 70 HF.

The procedures described in Example 1 were first used to form a solid TCMTB powder formulation having the above components and weight percentages. This powder was then compressed to form a tablet.

Example 3

A solid TCMTB tablet formulation was formulated as follows:

| Ingredients | Wt % (final formula) |
|---|---|
| TCMTB solution | 14.5% |
| MTC | 8.2% |
| Sodium sulfate, anhy. | 64.3% |
| Hi-Sil 233 (silica) | 2.0% |
| Stepwet DF-90 | 1.0% |
| Zeolex 7 | 10.0% |

The percentages are weight percentages of the final TCMTB formulation.

The TCMTB solution is a mixture of 92% by weight TCMTB 60, 7% by weight Tergitol XD, and 1% Casul 70 HF 1%. As recited above, TCMTB-60 contains TCMTB and dipropylene glycol monomethyl ether.

The procedures described in Example 1 were first used to form a solid TCMTB powder formulation having the above components and weight percentages. This powder was then compressed to form a tablet.

It was discovered that Talc (Nytal 300 hydrous magnesium silicate) and Zeolite A (from Ethyl Corporation) were not as good as Zeolex 7 in the formulation. However, these products can work well if the concentration of Hi-Sil 233 is increased in the formula. Hi-Sil 233 is a product from PPG Industries, Inc. (Pittsburgh, Pennsylvania).

Example 4

To assess the anti-bacterial effectiveness of liquid and solid TCMTB formulations a "cocktail" of bacterial organisms was employed to best simulate the mixed microflora normally encountered in these type of systems. The solid TCMTB tablet formulation from example 3 was employed as the solid formulation. The TCMTB solution employed was Busan 1009 which is a 30% TCMTB formulation and is commerically available from Buckman Laboratories, Inc., Memphis, Tenn. The organisms tested were, *Pseudomonas aeruginosa* ATCC 15442, *Staphylococcus aureus* ATCC 6538 and *Escherichia coli* ATCC 1224. Each organism was grown in Tryptone yeast extract agar (TGEA). For the assay the organisms were subcultured twice (24 hour subcultures) in TGEA buffered at pH 8.5. The assay growth from each organism was removed with a sterile cotton swab into a saline (9 ml) test tube. Each bacterial cell suspensions was standardized to a MacFarland 1 density. After standardization equal aliquots of each cell suspension were then dispensed into a separate test tube. The saline cell mixture was employed as the inoculum for the assay. One hundred (100) microliters was employed per 20 milliliters of synthetic cooling tower water. Each biocide was prepared as a stock solution in sterile deionized and water and diluted to added to the synthetic cooling water to the appropriate testing dosages (10, 20 & 50 ppm). The formulation of synthetic cooling tower water employed per liter was: typtone; 0.5 grams, dextrose; 0.5 grams sodium sulfate; 0.093 grams, sodium bicarbonate: 0.17 grams, sodium chloride: 0.26 grams, calcium chloride: 0.29 grams, magnesium sulfate: 0.60 grams. The medium was buffered at pH 8.5 with Tris-HCl: 1.23 grams, Tris-base; 5.13 grams. The test assay was carried out at 30° C. For the enumeration of surviving organisms the standard spread plate technique was utilized. All enumeration's were placed on TGEA and incubated at 37° C. for 24 hours. The controls did not contain any biocide. The results are displayed in FIG. 1. Based on the data obtained, no differences were observed that indicated that the liquid formulation of TCMTB/MTC was better than the solid formulation or vice-versa under the stated conditions. Some variability was observed due to experimental error and possible cell clumping. The solid formulation of TCMTB and MTC appears to be as effective as the liquid formulation. The benefits of having a solid over a liquid formulation include worker safety, convenience of use and unit dosing.

The claimed invention is:

1. A method of controlling the growth of at least one microorganism on a substrate in contact with an aqueous system and susceptible to the growth of at least one microorganism comprising the steps of:
   (a) adding to the aqueous system a solid formulation comprising TCMTB adsorbed onto a water-soluble salt carrier in n amount effective to control the growth of at least one microorganism on the substrate; and
   (b) contacting the substrate and the aqueous system containing said TCMTB formulation.

2. The method of claim 1, wherein the substrate is an animal hide, a textile, a wood product, or an agricultural product.

3. The method of claim 1, wherein the salt carrier matrix is selected from sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate and lithium chloride or mixtures thereof.

4. The method of claim 1, wherein the TCMTB formulation further comprises:
   an emulsifier in an amount of up to 20 percent by weight of the formulation; and
   an anti-caking agent in an amount of up to 30 percent by weight of the formulation; and
   a biocidal adjuvant in an amount of up to 50 percent by weight of the formulation.

5. The method of claim 1, wherein the TCMTB formulation further comprises:
   a biocidal adjuvant selected from the group consisting of germicides, fungicides, sanitizers, and oxidizing and/or halogen-release agents in an amount effective to control the growth of at least one organism.

6. The method of claim 1, wherein the TCMTB formulation is a powder.

7. The method of claim 1, wherein the TCMTB formulation is a tablet.

8. The method of claim 7, wherein the TCMTB formulation further comprises:
   a disintegration rate regulator in an amount of up to 20 percent by weight of the formulation
   an emulsifier in an amount of up to 20 percent by weight of the formulation;
   an anti-caking agent in an amount of up to 30 percent by weight of the formulation; and
   a biocidal adjuvant in an amount of up to 50 percent by weight of the formulation.

9. The method of claim 1, wherein the TCMTB formulation is contained within a water-soluble container.

10. The method of claim 9, wherein the water-soluble container is a water-soluble bag comprised of polyvinyl alcohol, polyvinyl acetate, methyl cellulose, hydroxyethyl cellulose, carboxymethyl cellulose, sodium carboxymethyl-hydroxyethyl cellulose, polyvinyl pyrrolidone, poly(alkyl) oxazoline, film-forming derivatives of polyethylene glycol or mixtures thereof.

11. The method of claim 10, wherein the water-soluble bag is selected from the group consisting of polyvinyl alcohol, polyvinyl acetate and mixtures thereof.

12. The method of claim 10, wherein the water-soluble container is contained within a moisture proof outerwrap.

13. The method of claim 1, wherein the aqueous system is a tanning liquor and the substrate is an animal hide.

14. The method of claim 13, wherein the tanning liquor is selected from a pickling liquor, a chrome-tanning liquor, a vegetable-tanning liquor, a post-tan washing liquor, a retanning liquor, a dye liquor, and a fat liquor.

15. The method of claim 13, wherein the animal hide is a brine-cured hide or skin and the TCMTB formulation is used at a level of about 225–1150 grams per 1000 lbs of green fleshed hides or skins.

16. The method of claim 13, wherein the animal hide is a chrome or vegetable-tanned hide and the TCMTB formulation is used at a level of about 225 grams to 1360 grams per 450 kilograms of white weight stock.

17. The method of claim 1, wherein the substrate is a textile, the aqueous system is a bath, and the contacting step comprises dipping the textile into the bath.

18. The method of claim 1, wherein the substrate is a textile and the contacting step comprises spraying the textile with the aqueous system containing said TCMTB formulation.

19. The method of claim 1, wherein the substrate is lumber, the aqueous system is a bath, the contacting step comprises dipping the lumber into the bath, and the method further comprises the step of drying the lumber after the contacting step.

20. The method of claim 1, wherein the substrate is a lumber, the contacting step comprises spraying the lumber with the aqueous system containing said TCMTB formulation, and the method further comprises the step of drying the lumber after the contacting step.

21. The method of claim 1, wherein the substrate is a seed or a plant, substrate, the aqueous system is a bath, the contacting step comprises dipping the seed or plant into the bath, and the method further comprises the step of drying the seed or plant after the contacting step.

22. The method of claim 1, wherein the substrate is a seed or plant, the contacting step comprises spraying the seed or plant with the aqueous system containing said TCMTB formulation, and the method further comprises the step of drying the seed or plant after the treating step.

* * * * *